US008691282B2

(12) United States Patent
Moest et al.

(10) Patent No.: US 8,691,282 B2
(45) Date of Patent: Apr. 8, 2014

(54) METHOD FOR PRODUCING PANCREATIN PELLETS

(75) Inventors: Thomas Moest, Uetersen (DE); Walter Doleschal, Uetersen (DE); Manfred Kurfürst, Moorrege (DE)

(73) Assignee: Nordmark Areneimittel GmbH & Co. KG, Uetersen (DE)

( * ) Notice: Subject to any disclaimer, the term of this patent is extended or adjusted under 35 U.S.C. 154(b) by 0 days.

(21) Appl. No.: 13/368,415

(22) Filed: Feb. 8, 2012

(65) Prior Publication Data
US 2012/0213857 A1 Aug. 23, 2012

(30) Foreign Application Priority Data

| Feb. 17, 2011 | (EP) | 11154829 |
| Mar. 22, 2011 | (EP) | 11159267 |
| Mar. 30, 2011 | (DE) | 20 2011 000 728 U |
| May 31, 2011 | (EP) | 11168323 |
| Jul. 27, 2011 | (EP) | 11175546 |

(51) Int. Cl.
*A61K 9/16* (2006.01)
*A61K 9/50* (2006.01)

(52) U.S. Cl.
CPC ............................. *A61K 9/1688* (2013.01); *A61K 9/5089* (2013.01)
USPC ........................... 424/490; 424/400; 514/1.1

(58) Field of Classification Search
None
See application file for complete search history.

(56) References Cited

U.S. PATENT DOCUMENTS

| 2,189,948 | A | 2/1940 | Griffith |
| 3,313,705 | A * | 4/1967 | Abel Henry ............... 424/94.21 |
| 4,280,971 | A | 7/1981 | Wischniewski |
| 5,378,462 | A | 1/1995 | Boedecker |
| 6,270,723 | B1 | 8/2001 | Laugharn |
| 2005/0250817 | A1 | 11/2005 | Shlieout |
| 2007/0148152 | A1 | 6/2007 | Shlieout |
| 2011/0052706 | A1 | 3/2011 | Moest |
| 2011/0268844 | A1 | 11/2011 | Ramsch |
| 2011/0293590 | A1 | 12/2011 | Kurfurst |

FOREIGN PATENT DOCUMENTS

| EP | 0436110 | 7/1991 |
| SU | 271472 | 7/1968 |
| WO | WO 2006/044529 A1 | 4/2006 |
| WO | WO 2008/127567 A1 | 10/2008 |
| WO | PCT/EP2009/006216 | 8/2009 |
| WO | PCT/EP2009/000566 | 12/2011 |

OTHER PUBLICATIONS

USPTO Office Action, mailed Jan. 13, 2012, issued in U.S. patent publication No. US 2011/0052706.
USPTO Office Action, mailed Mar. 23, 2012, issued in U.S. patent publication No. US 2011/0052706.
USPTO Office Action, mailed Jan. 7, 2013, issued in U.S. patent publication No. US 2011/0052706.
USPTO Office Action, mailed Nov. 27, 2012, issued in U.S. patent publication No. US 2011/0293590.
USPTO Office Action, mailed Jul. 10, 2013, issued in U.S. patent publication No. US 2011/0268844.

* cited by examiner

*Primary Examiner* — Bethany Barham
(74) *Attorney, Agent, or Firm* — Nash and Titus, LLC

(57) ABSTRACT

In order to avoid compromising the pharmacological effect of pancreatin caused by the addition of auxiliary materials or binding agents, a pancreatin pellet having a 100% pancreatin content consists exclusively of pancreatin with a residual moisture content of less than 3% by weight, preferably less than 1% by weight or less than 0.5% by weight.

12 Claims, 2 Drawing Sheets

METHOD FOR PRODUCING PANCREATIN PELLETS

This application and the invention described herein claim priority from the following foreign applications: German application DE 20 2011 000 728.6 (filed Mar. 30, 2011); European application EP 11 154 829.3 (filed Feb. 17, 2011); European application EP 11 159 26.1 (filed Mar. 22, 2011); European application EP 11 168 323.1 (filed May 31, 2011); and European application EP 11 175 546.8 (filed Jul. 27, 2011). The contents of all of these documents are incorporated herein in their entirety.

BACKGROUND OF THE INVENTION

The invention relates to pancreatin pellets, in particular to pancreatin micropellets, and to a process for their production.

Pancreatin is the term used to define the mixture of enzymes extracted from the pancreatic gland, essentially consisting of lipases, amylase and proteases. The primary starting material for the production of pancreatin is fresh or frozen pig's pancreas, from which only water and fat was originally removed in order to produce pancreatin. Because of the sensitivity of the enzymes, however, processes have been developed in order to obtain the pancreatin in as gentle a manner as possible. A suitable process is described in DE 32 48 588 A1.

Pancreatin is used in particular as an active ingredient for the treatment of digestive disorders due to pancreatic insufficiency. Pancreatin is primarily employed in the dried form as an oral therapeutic agent. It has been observed in this regard that the therapeutic effectiveness of pancreatin administration can be improved if the active ingredient is administered in the form of pellets or micropellets.

Typically, the production of pancreatin pellets involves supplementing the pancreatin with auxiliary materials and binding agents and mixing those components until a homogeneous mixture is obtained. The homogeneous mixture is then introduced into an extruder in which the mixture is transformed into a strand-like extrudate. Finally, the extrudate is introduced into a spheronizer, possibly with the addition of further auxiliary materials, in which the extrudates are transformed into spherical pellets. The pellets are then dried and screened to sort out screened fractions of pellets which are above or below a predetermined size range. The pellets obtained thereby can then be coated with a coating of enteric material.

Upon production, pancreatin precipitates out moistened with solvent and is then normally dried and ground. However, it is disadvantageous to moisten and dry said material several times more in order to shape it, for example upon granulation and spheronization. This takes time and energy and frequently results in loss of quality as the highly sensitive enzymes are damaged.

Until now, pancreatin pellets have been produced from dry pancreatin powder by wet granulation. Normally, auxiliary materials and binding agents are still required in this regard. A process for the production of pancreatin pellets consists in moistening powdered pancreatin with a solvent mixture and shaping it with an extruder into cylindrical raw pellets. The extrudates then also have to be cut to a length of 1.5 mm to 1.7 mm, for example. After drying, those raw pellets are spheronized with a moist pancreatin/coating mixture and then dried again.

A further process for the production of pancreatin micropellets is described, for example, in EP 0 583 726 A2. In that process, prior to extrusion, 100 parts by weight of pancreatin is mixed with 15 to 50 parts by weight of polyethylene glycol 4000 and 10 to 30 parts by weight of an alcohol. The alcohol, for example propanol, is intended to provide the mixture with an extrudable consistency. Prior to transfer into the spheronizer, the extrudates obtained by extrusion are then supplemented with 1.5 to 5 parts by weight of paraffin and a further 1.5 to 10 parts by weight of alcohol. The pellets obtained have a pancreatin content of 65% to 85% by weight, and so the pellets contain at least 15% by weight of auxiliary materials and binding agents.

The auxiliary materials and binding agents required for extrusion may, however, have unwanted side effects. For this reason, constant vigilance is required when selecting the auxiliary materials and binding agents. As an example, it has been observed that the current usual practice of adding mineral oils can no longer be assumed to be immaterial.

For this reason, EP 1 931 317 B1 proposes a process for producing pancreatin pellets without the addition of paraffin. The pancreatin pellets obtained in this case contain 10% to 95% by weight of pancreatin, with at least 5% by weight of auxiliary materials and binding agents such as polyethylene glycol.

However, objections can be expected to be raised against any type of additive on reasoned or even on arbitrary grounds. It would thus be desirable to provide pancreatin in a form which on the one hand can be administered orally and on the other hand is, as far as possible, free from any additives. In addition, a pancreatin concentration of 100% also means that the volume to be administered is a minimum per fixed dose; this makes it easier for the patient to take.

U.S. Pat. No. 4,280,971 A1 discloses a process for the production of pancreatin pellets in which a pliable mass containing a pancreatin powder and an enzyme-friendly solvent is extruded on an extruder, if necessary with cooling, the extrudate is divided into extrudate fragments, dried and then processed further using known methods, for example by applying coatings to the extrudate fragments. However, the process proposes two drying steps, which is not economical, since a mixture of magnesium stearate, pancreatin and isopropanol is produced which is processed on an extruder with bores and cutting equipment to produce extrudates of a predetermined length. The raw pellets obtained thereby are dried in a first step. Next, the raw pellets are spheronized to spherical pellets by applying an isopropanolic solution of polyvinyl pyrrolidone and pancreatin which are then dried further in a second drying step. In that process, it is assumed that the end product has a relatively high residual moisture content because considerable quantities of solvents are employed, but no information is provided to this effect. In addition, the pellets produced have a pancreatin content of more than 65% to 85% by weight, so the pellets may contain up to 15% by weight of auxiliary materials and binding agents; in addition, the pancreatin is initially mixed with magnesium stearate. Furthermore, the process is multi-staged and thus complicated.

EP 0 436 110 A1 discloses a process for the production of spherical pancreatin particles which is characterized by rotating a moist pancreatin mass together with a solvent about a first axis and simultaneously reducing the size of the mass with the aid of knives which rotate about a second axis, wherein a portion of the solvent is removed; the first and the second axes are at an angle to each other, wherein the two axes are arranged perpendicular to each other, so that the mass is subjected to a rolling motion. Overall, the transformation of an already developed and improved pancreatin mass, which is still moistened with solvent, however, into a galenical form is disclosed. The solvent is acetone. The disclosed process for the production of pancreatin particles proposes comminuting the pancreatin mass with the aid of knives, whereby only a portion of the solvent is removed.

U.S. Pat. No. 5,378,462 concerns a pancreatin micropellet core which can be coated with an enteric film and has a pancreatin content of 60% to 85% by weight. The pellet cores are spherical to ellipsoidal in shape, with a diameter or minor axis in the region of 0.7 to 1.4 mm. The pellet cores have a particle size distribution in which at least 80% of the pellet cores have a ratio of the minor axis to the major axis in the region of 1:1 to 1:2. This is intended to result in an improved process by means of which novel pancreatin micropellets coated with an enteric film can be produced with a high bulk density and which have a small particle size which guarantees their successful passage through the pylorus.

DE 20 2010 004 926 U1 discloses Pancreatin pellets which consist exclusively of Pancreatin and are obtained by the following procedure: the pancreas glands originating from pigs or cattle are first comminuted and subjected to autolysis. By filtering the intermediate product thus obtained, a screen filtrate is produced. The enzymes contained in the screen filtrate are precipitated. The mixture thus obtained is filtered and a filter cake is produced which is ground and vacuum-dried until it has a residual moisture content of 0.1 to 03% by weight. Since the extrudable filter cake mass has a residual moisture content/organic solvent residues of approximately 50%, the filter cake is subjected to a heat treatment at 80° C. or less. The heat-treated filter cake is then extruded and then spheronised to give spherical, elliptical or drop-like pellets. In this production method, the processing of the filter cake in the extruder is associated with difficulties insofar as the filter cake exhibits pseudoplastic behaviour to the extent that the filter cake exhibits high flowability under shear load, and therefore difficulties are encountered with further shaping to the point that shaping may no longer be possible and therefore additional binders have to be used.

SUMMARY OF THE INVENTION

The aim of the present invention is to provide pancreatin pellets with improved properties and an improved and economical process for their production, wherein the pellets can be produced without added auxiliary materials, binding agents, additives or any other processing aids so that the pharmacological effect of the pancreatin is not compromised, keeping the pancreatin in as active a form as possible, and also facilitating oral administration of the pellets. Furthermore, pellets with a pancreatin content of 100% and with a high pancreatin quality as regards the enzyme density and with as small a residual moisture content as possible should be able to be produced using a process in which only a single drying procedure is proposed, which is carried out at the end of the process, in order to remove environmental moisture that has been taken up during production.

Furthermore, a pharmaceutical composition which contains the pancreatin pellets of the invention, as well as the use of the pancreatin pellets, are proposed.

This aim is achieved by means of the features of the invention in all of its various embodiments as described in detail here.

DETAILED DESCRIPTION OF THE PREFERRED EMBODIMENTS

Figure 1:
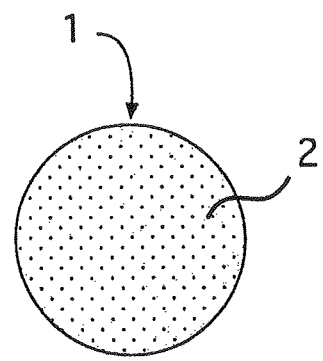
FIG. 1 shows a sectional view of a first embodiment of a pancreatin pellet of the invention, formed exclusively from pancreatin.

According to the invention, pancreatin pellets are provided which are exclusively formed from pancreatin. The pancreatin pellets of the invention thus consist of 100% pancreatin and contain no auxiliary materials or binding agents. The pharmaceutical load is 100%. The invention also encompasses pellet cores with a pancreatin content of 100% exclusive of a coating, wherein a coating is also possible.

The pancreatin pellets, in particular micropellets, of the invention, preferably containing pancreatin obtained from the pancreas of a mammal and having a spherical, ellipsoidal or drop shape as well as an axis in the range 0.5 mm to 2.5 mm, and having a pancreatin content of 100%, are produced using the following succession of steps:

a) comminuting pancreas glands originating from pigs or cattle and carrying out an autolysis;

b) obtaining a screen filtrate containing enzymes by filtering the intermediate product obtained after step a);

c) precipitating the enzymes out of the screen filtrate;

d) filtering the mixture obtained after step c) to obtain a filter cake;

e) cooling the filter cake obtained after step d) to −10° C. to −40° C., preferably to −30° C., to obtain a sufficient plasticity;

f) extruding the cooled filter cake obtained in step e), whilst excluding additives and/or binding agents, in order to form extrudates, wherein the extrudable filter cake mass contains residual moisture or organic solvent residues which are of the order of 30% to 50%, in particular 40%;

g) spheronizing, whilst excluding additives and/or binding agents or other auxiliary materials, to obtain spherical, elliptical or drop-shaped pellets;

h) vacuum drying the pellets obtained until the residual moisture content is less than 3% by weight, preferably less than 1% by weight or less than 0.5% by weight, so that a dried pancreatin end product is obtained with a residual moisture content of less than 3% by weight, preferably less than 1% by weight or less than 0.5% by weight.

The pancreatin pellets of the invention have the advantage that the pharmacological effect of the pancreatin is not compromised due to the addition of auxiliary materials or binding agents or both.

The term "pellet" as used in the present invention means a body with a spherical, ellipsoidal or drop-like shape, wherein the diameter of the sphere or the minor axis is in the range 0.5 mm to 2.5 mm.

The pellet produced in accordance with the process of the invention, in particular a micropellet, has a 100% pancreatin content and has the particular property of a residual moisture content of less than 3% by weight, preferably less than 1% by weight or less than 0.5% by weight. Extrusion is carried out without the addition of a pelletization processing aid.

Step e), in which the filter cake obtained after step d) is cooled, is particularly advantageous. Cooling is an important step of the process, as it surprisingly results in an improvement in the viscosity of the structure and maintains the plastic deformability of the filter cake. Further processability of the filter cake in the extruder after step f) of the process is difficult since a non-cooled filter cake has structural viscosity such that under shear loads, the filter cake has high fluidity and is no longer malleable—rheologically speaking, it exhibits plastic flow with Casson flow characteristics and partial rheodestruction. Surprisingly, this structural viscosity is sustainably improved by cooling to −10° C. to −40° C., preferably to −30° C., so that even under shear loads, the desirable and necessary plastic deformability is retained. Radial extruders with extrudate cutting equipment can be used to produce cylindrical extrudates which can be shaped into pellets by spheronizing using rotating disks (spheronizer). It is known that pellet production using extrusion/spheronization is a (semi)-continuous producing process. While the extrusion step can be carried out continuously, spheronization of the extrudates can be carried out in batches in spheronizers, resulting in pharmaceutical loads of up to 95%. This also means that the addition of a pelletization processing aid for extrusion is indispensable.

In contrast, in accordance with the process of the invention, on extrusion, pharmaceutical loads of 100% are surprisingly obtained. Pelletization processing aids are not employed.

The subject matter of the dependent claims concern further advantageous embodiments of the invention.

The scope of the invention includes the fact that the pancreatin pellet is a micropellet.

The pancreatin has preferably been obtained from the pancreas of a mammal, preferably from pancreases from pigs or cattle. Pellet production is integrated into the process for obtaining pancreatin. Adding a specific processing aid for the production of a plastic mass, as required in the prior art for pelletization using an extruder, is thus not required.

The process of the invention for the production of pellets, in particular micropellets, from pancreatin consists of the following steps of the process:
a) comminuting pancreas glands originating from pigs or cattle and carrying out an autolysis;
b) obtaining a screen filtrate containing enzymes by filtering the intermediate product obtained after step a);
c) precipitating the enzymes out of the screen filtrate;
d) filtering the mixture obtained after step c) to obtain a filter cake;
e) cooling the filter cake obtained after step d) to −10° C. to −40° C., preferably to −30° C., to obtain a sufficient plasticity; extruding the cooled filter cake obtained in step e), whilst excluding additives and/or binding agents, in order to form extrudates, wherein the extrudable filter cake mass contains residual moisture or organic solvent residues which are of the order of 30% to 50%, in particular 40%;
g) spheronizing, whilst excluding additives and/or binding agents or other auxiliary materials, to obtain spherical, elliptical or drop-shaped pellets;
h) vacuum drying the pellets obtained until the residual moisture content is less than 3% by weight, preferably less than 1% by weight or less than 0.5% by weight, so that a dried pancreatin end product is obtained with a residual moisture content of less than 3% by weight, preferably less than 1% by weight or less than 0.5% by weight.

The filter cake obtained following the succession of steps of the process is surprisingly capable of being extruded and spheronized immediately without further additives and/or binding agents. Afterwards, the pellets obtained are dried.

The filter cake has sufficient plasticity to be able to extrude the filter cake to form extrudates. After extrusion, spheronization is carried out, also without adding additives and/or binding agents or any other auxiliary materials. This produces spherical, elliptical or drop-shaped pellets which can be used as they are or as cores provided with a coating. Next, the pellets obtained are vacuum dried until the residual moisture content is less than 3% by weight, preferably less than 1% by weight or less than 0.5% by weight. The final pancreatin product obtained thus has a residual moisture content of less than 3% by weight, preferably less than 1% by weight or less than 0.5% by weight. This very low residual moisture content is a characterizing property of these pellets or micropellets and thus provides the distinction over known pancreatin pellets.

In accordance with a further embodiment of the invention, the pellet consists of a core with a pancreatin content of 100%. This core is not coated with an enteric coating; however, it can also be provided with an enteric coating.

According to the invention, a pancreatin pellet is thus provided which has a core with or without a coating, wherein the core is exclusively formed from pancreatin. The core consists of 100% pancreatin and contains no auxiliary materials or binding agents. In contrast, the coating may be formed from at least one auxiliary material and/or at least one binding agent.

In accordance with a further embodiment of the invention, the coating surrounding the pancreatin core consists of an enteric material. The pellets produced are coated so that they are resistant to stomach acid and to ensure that they only dissolve in the digestive tract. The enteric coating is applied without a solvent with a dispersive film-forming agent based on polymethacrylic acid. The coated pellets from screen fractions of between 0.5 to 2.5 mm mesh are packaged into capsules.

The gentle processing of the process of the invention for the production of pancreatin pellets and the use of pure, undiluted active ingredients results in a pancreatin product with high specific activity, making it possible to produce high dose pancreatin pharmaceuticals in relatively small, patient-friendly capsule sizes. The maximum capsule capacity for the pancreatin pellet mass is 265 mg, 475 mg, 570 mg or 680 mg, depending on the capsule size.

In accordance with another embodiment, the coating consists of a first, inner layer which surrounds the core formed from pancreatin, and a second, outer layer. Preferably, the first layer is formed from at least one auxiliary material and/or at least one binding agent. The second layer is preferably formed from an enteric material.

The proportion by weight of auxiliary materials and binding agents on the pancreatin pellet may be in the range 5% to 30% by weight. The proportion by weight of enteric material on the pancreatin pellet may be in the range 10% to 30% by weight.

The auxiliary materials or binding agents which enclose the core formed from pancreatin act to provide the core with cohesiveness, for example during storage and transport of the pellets, and thus prevent mechanical or chemical destruction of the core. The auxiliary materials and binding agents used must be pharmacologically acceptable.

Suitable pharmacologically acceptable auxiliary materials which can form the coating or the inner layer of the coating, if appropriate together with the binding agents described below, include, for example, fillers, desiccants, lubricants, disintegration agents and colorants. This list is not exhaustive; other auxiliary materials which are known to the skilled person may, of course, be employed.

Examples of suitable fillers are selected from the group comprising calcium phosphate, microcrystalline cellulose, dextran, dextrin, precipitated calcium carbonate, hydrated silicon dioxide, kaolin, lactose, mannitol, corn starch, polyvinyl pyrrolidone, sorbitol, talc and mixtures thereof.

Examples of suitable desiccants are selected from the group comprising colloidal silicic acid, talc and mixtures thereof. Examples of suitable disintegration agents are selected from the group comprising alginic acid, amylose, calcium alginate, calcium carbonate, sodium bicarbonate, cross-linked polyvinyl pyrrolidone, silicic acid, sago starch, starches and mixtures thereof. Suitable lubricants are selected from the group comprising, for example, calcium or magnesium stearate, starches, stearic acid, talc and mixtures thereof.

Examples of suitable pharmacologically acceptable binding agents which may form the coating or the inner layer of the coating, if appropriate together with the auxiliary materials described hereinabove, are compounds which are selected from the group comprising hydroxypropylmethyl cellulose, polyethylene glycols such as polyethylene glycol 1500, polyethylene glycol 2000, polyethylene glycol 3000, polyethylene glycol 4000, polyethylene glycol 6000, polyethylene glycol 8000, polyethylene glycol 10000, polyoxyethylene, polyoxyethylene-polyoxypropylene copolymers, and mixtures thereof. This list is not exhaustive; other binding agents which are known to the skilled person may, of course, be used. Examples of suitable colorants are food colorants, in particular food colorants which are listed in the German Arzneimittelfarbstoffverordnung [AMFarbV-Pharmaceutical Colouring Agents Regulations]. These lists are not exhaustive; other auxiliary materials which are known to the skilled person may, of course, be employed.

The coating formed from auxiliary materials and/or binding agents or the inner layer of the coating may be formed using known techniques, for example in a fluidized bed apparatus or a bead coater. When carrying out coating in a bead coater, the pellets, which consist exclusively of pancreatin, are introduced into the bead coater and sprayed with a pre-prepared, homogeneous mixture of binding agent and auxiliary materials.

The enteric coating prevents the pancreatin from being destroyed in the stomach by reaction of the stomach acid with the acid-labile components of the pancreatin, in particular the lipases. After passing through the stomach and the change in the pH on entering the small intestine, the protective film formed by the enteric coating around the core of pancreatin dissolves, so that the pancreatin is released. The enteric material has to be stable at a pH of up to 5.5 and only release the pancreatin at a pH of 5.5 or above, preferably 6 and above.

Suitable enteric materials which are used to form coatings for the pellets are known in the art. Normally, such coatings contain a film-forming agent, normally a plasticizer and in some cases a release agent. Examples of suitable film-forming agents are selected from the group comprising hydroxypropylmethyl cellulose acetate succinate (HPMCAS), hydroxypropylmethyl cellulose phthalate (HPMCP), cellulose acetate phthalate (CAP), polyvinylacetate phthalate (PVAP), methacrylic acid—methyl methacrylate copolymers and methacrylic acid—ethyl acrylate copolymers, and mixtures thereof. This list is not exhaustive; other film-forming agents known to the skilled person may, of course, be employed.

If in addition to a film-forming agent, the enteric material contains a plasticizer, then its proportion with respect to the film-forming agent is in the range 1% to 20% by weight. Preferred plasticizers are mono-alcohols containing 12 to 30 carbon atoms, such as cetyl alcohol (1-hexadecanol) or stearyl alcohol (1-octadecanol), as well as polyethylene glycols and triethyl citrate and mixtures thereof. This list is not exhaustive; other plasticizers which are known to the skilled person may, of course, be employed.

If the enteric material contains a release agent in addition to the film-forming agent and an optional plasticizer, then its proportion is in the range 0.5% to 5% by weight with respect to the film-forming agent. Examples of release agents are talc and dimethicone. This list is not exhaustive; other release agents which are known to the skilled person may, of course, be employed.

In order to produce the coating formed from the enteric material, the film-forming agent, optional plasticizer and/or release agent can be dissolved or dispersed in a solvent in known manner. After the coating has been formed, the solvent will be removed, for example by drying. Suitable solvents are selected from the group comprising water, acetone, alcohols containing 1 to 5 carbon atoms such as methanol, ethanol, n- and iso-propanol, or n- and tert-butanol, and mixtures thereof.

The enteric coating may be formed using known techniques, for example in a fluidized bed apparatus or a bead coater. When coating using a bead coater, the pellets, either directly formed from 100% active ingredient or already coated with a coating of auxiliary materials, are introduced into the bead coater and the enteric material is sprayed on.

The pancreatin pellets of the invention may be in the shape of drops or be spherical in shape. Preferably in this case, the core is spherical in shape, while the coating may provide the pancreatin pellet with a droplet shape, which makes dosing of the pellets easier, for example from dropping bottles.

A drop shape has the advantage that when falling, the pellets orientate themselves in one direction. This allows easy counting of the drop-shaped pancreatin pellets from a storage container such as a dropping bottle.

The pancreatin pellets of the invention, in particular micropellets, are suitable for the production of pharmaceuticals.

The pancreatin pellets of the invention may be used for the production of a pharmaceutical composition. Preferably, the pharmaceutical composition contains the pancreatin pellets of the invention in a pharmacologically effective dose which is suitable for oral administration and is provided for the treatment and/or prophylaxis of digestive disorders, acute pancreatitis, chronic pancreatitis, exocrinal pancreatic insufficiency, diabetes mellitus, in particular type I or type II, and cystic fibrosis.

The pancreatin pellets of the invention are also suitable for the production of foodstuffs or nourishment or as a food supplement.

The invention will now be described with the aid of examples which in no way limit the invention, made with reference to the accompanying drawings.

The first embodiment of a pancreatin pellet 1 of the invention, shown in FIG. 1, shows that this pellet 1 is formed exclusively from pancreatin, 2. It does not have a coating.

Figure 2:
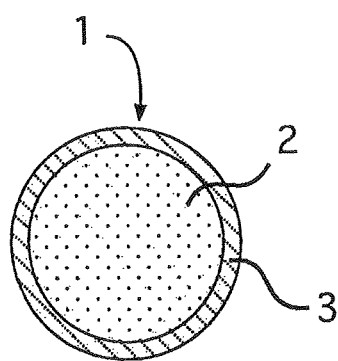
FIG. 2 shows a sectional view of a second embodiment of a pancreatin pellet of the invention with a pancreatin core and a single-layered coating.

In contrast, the second embodiment of a pancreatin pellet 1 of the invention, shown in FIG. 2, has a core 2 and a single-layered coating 3. The core 2 consists exclusively of pancreatin. The coating 3 preferably consists of an enteric material. Furthermore, the coating may contain auxiliary materials, for example binding agents. The coating 3 acts to provide the pancreatin core 2 with cohesiveness and can, for example, prevent mechanical or chemical destruction of the core 2; in particular, it protects against attack by stomach acid.

The uncoated pellet cores are mechanically stable and can be coated directly.

Figure 3:
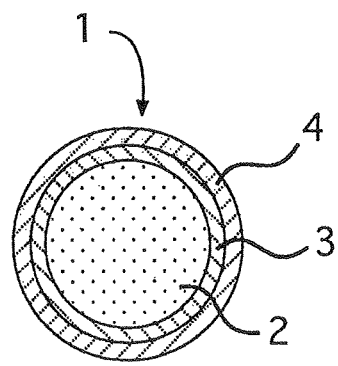
FIG. 3 shows a sectional view of a third embodiment of a pancreatin pellet of the invention with a pancreatin core and a double-layered coating.

The third embodiment of the pancreatin pellet of the invention, shown in FIG. 3, has a double-layered coating. The inner coating 3 surrounds the core 2 formed from pancreatin. In this manner, the pancreatin core is cohesive and protected against mechanical or chemical destruction. The outer layer 4 consists of an enteric material.

Figure 4:
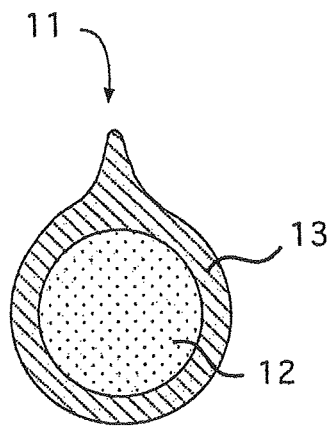
FIG. 4 shows a sectional view of a fourth embodiment of a pancreatin pellet of the invention with a pancreatin core and a single-layered, drop-shaped coating.
Figure 5:
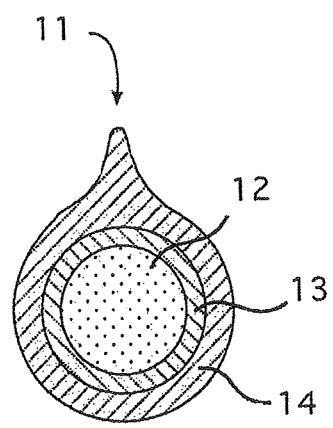
FIG. 5 shows a sectional view of a fifth embodiment of a pancreatin pellet of the invention with a pancreatin core and a double-layered, drop-shaped coating.

In FIGS. 4 and 5, the coating is drop-shaped. In the embodiment shown in FIG. 4, the pancreatin pellet 11 has a single-layered coating 13 which is drop-shaped, which surrounds the spherical core 12 formed exclusively from pancreatin. The coating 13 in this case consists of auxiliary materials, for example binding agents. In FIG. 5, the coating is double-layered and has an inner layer 13 and an outer layer 14. Only the layer 14 is drop-shaped, while the inner layer 13 is spherical. The inner layer 13 consists of auxiliary materials, for example binding agents, which provide the core 13 with cohesiveness. The outer layer 14 consists of an enteric material. The droplet shape, in particular that of the pancreatin micropellet, allows, inter alia, for individual dosing of pellets from a dropping bottle, for example.

The example below demonstrates a possibility for the production of pellets from pancreatin, wherein a cooling step is carried out in order to extrude the filter cake.

The starting material is a pancreatin filter cake containing solvent, wherein the solvent contained in the filter cake is approximately 70% to 85%, preferably 75% to 80% isopropanol or acetone; isopropanol is preferred to acetone; the remainder is water.

The moist 40% to 70% by weight pancreatin filter cake is initially coarsely ground, for example by means of a cutter or gentle extrusion without a large pressure rise through large nozzles 5 to 8 mm in diameter, then cooled to −10° C. to −40° C., preferably to −30° C. The cooling changes the consistency of the mass so that it becomes easy to extrude. In addition, the enzymes of the pancreatin are stabilized thereby. The extrusion proper is then carried out using known processes on machines such as a screw extruder or pan mill, preferably through round nozzles with a diameter in the range 0.5 mm to 5 mm, preferably in the range 1.0 mm to 2.5 mm. The extrudates may be cut, but do not have to be cut. They can be shaped directly with a commercially available spheronizer into spherical pellets with a smooth surface. By warming the pellets externally, the surface becomes softer and deformable, so that a near spherical (spheroidal) shape is produced with a regular smooth surface (no peaks and troughs). These pellets are then dried and contain only pure pancreatin. The pellets thus produced can readily be further processed to finished pharmaceuticals by enteric coating and, for example, by filling into hard gelatin two-piece capsules.

The process of the invention is economical as there is only one drying step since the moist filter cake precipitated out during production of the pancreatin is used directly.

The high active ingredient density produced by avoiding repeated drying with corresponding loss of enzyme and by dispensing with auxiliary materials and binding agents means that correspondingly smaller pharmaceutical forms can be produced, which are easier for the patient to swallow, or alternatively, the same shape and size can provide a higher dose.

List of reference numerals

| | |
|---|---|
| 1 | spherical pancreatin pellet |
| 2 | pancreatin |
| 3 | coating formed from auxiliary materials or binding agent |
| 4 | coating formed from enteric material |
| 11 | drop-shaped pancreatin pellet |

-continued

List of reference numerals

| | |
|---|---|
| 12 | pancreatin |
| 13 | coating formed from auxiliary materials and binding agent |
| 14 | coating formed from an enteric material |

The invention claimed is:

1. A method for producing a pancreatin pellet and/or micropellet, which pellet and/or micropellet has a spherical, ellipsoidal or drop shape, has an axis in the range 0.5 mm to 2.5 mm,
comprising the steps of
a) comminuting the pancreases of pigs or cattle and conducting autolysis;
b) obtaining a screen filtrate by filtration of the product obtained in step a);
c) precipitating the enzymes from the screen filtrate;
d) filtering the product of step c) to obtain a filter cake;
e) cooling the filter cake to a temperature between about −10° C. to about −40° C., to obtain a sufficient plasticity;
f) extruding the cooled filter cake, in the absence of additives and/or binding agents, to form extrudates, wherein extrudable filter cake mass contains residual moisture or organic solvent residues between about 30% to about 50% by weight;
g) spheronizing the extrusion obtained in step (f), in the absence of additives and/or binding agents or auxiliary substances, so as to obtain spherical, elliptical or drop-shaped pellets; and
h) vacuum drying the pellets obtained in step (g) until a residual moisture content of less than 3% by weight is obtained, so that a dried pancreatin product is produced with a residual moisture content of less than 3% by weight.

2. The method according to claim 1, wherein the pellet produced has a pancreatin content of 100%.

3. The method according to claim 1, which comprises the further step of coating the pancreatin pellet, so as to form a pancreatin core having a coating.

4. The method according to claim 3, wherein the coating comprises an enteric material.

5. The method according to claim 3, wherein the coating consists of pancreatin or is formed from auxiliary materials or binding agents.

6. The method according to claim 3, wherein the coating has a first, inner layer which surrounds the pancreatin core, and further has a second, outer layer.

7. The method according to claim 6, wherein the first layer is formed from auxiliary materials or binding agents.

8. The method according to claim 6, wherein the second layer is formed from an enteric material, wherein the pellet is drop-shaped or spherical in shape.

9. The method according to claim 1, wherein in step (e) the filter cake is cooled to about −30° C.

10. The method according to claim 1, wherein in step (f) extrudable filter cake mass contains residual moisture or organic solvent of about 40% by weight.

11. The method according to claim 1, wherein in step (h) the residual moisture content obtained is less than 1% by weight, so that a dried pancreatin product is produced with a residual moisture content of less than 1% by weight.

12. The method according to claim 1, wherein in step (h) the residual moisture content obtained is less than 0.5% by weight, so that a dried pancreatin product is produced with a residual moisture content of less than 0.5% by weight.

* * * * *